US007011605B2

(12) United States Patent
Shields (10) Patent No.: US 7,011,605 B2
(45) Date of Patent: Mar. 14, 2006

(54) THERAPEUTIC EXERCISE SYSTEM AND METHOD FOR A PARALYZED AND NONPARALYZED NEUROMUSCULOSKELETAL TRAINING SYSTEM

(75) Inventor: Richard Shields, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 10/518,420

(22) PCT Filed: Jun. 18, 2003

(86) PCT No.: PCT/US03/19344

§ 371 (c)(1),
(2), (4) Date: May 25, 2005

(87) PCT Pub. No.: WO03/105744

PCT Pub. Date: Dec. 24, 2003

(65) Prior Publication Data

US 2005/0209049 A1   Sep. 22, 2005

(51) Int. Cl.
*A63B 2/00* (2006.01)
(52) U.S. Cl. .................... 482/8; 607/2; 607/48
(58) Field of Classification Search ............. 482/1–9, 482/900–902, 51; 607/48–49, 77, 78, 1, 607/2
See application file for complete search history.

(56) References Cited

U.S. PATENT DOCUMENTS

| 4,863,157 A | | 9/1989 | Mendel et al. |
| 4,947,836 A | | 8/1990 | Laenger et al. |
| 5,328,424 A | * | 7/1994 | Greco .................... 482/73 |
| 5,961,541 A | | 10/1999 | Ferrati |
| 6,456,885 B1 | | 9/2002 | Shiba et al. |
| 6,876,883 B1 | * | 4/2005 | Hurtado .................. 607/48 |

* cited by examiner

*Primary Examiner*—Glenn E. Richman
(74) *Attorney, Agent, or Firm*—Needle & Rosenberg, P.C.

(57) ABSTRACT

The present invention relates to an exercise method for the elderly, individuals with impaired joint control, and a system for individuals who are suffering from muscular paralysis and who may or may not be confined to a wheelchair by the implementation of an exercise device that can safely provide actively supported standing exercise options to persons who either have limited physical mobility or complete loss of mobility due to muscular paralysis. An embodiment of the present invention relates to a standing wheelchair that is used to passively restrain an operator. The axial and tangential loads that are exerted upon the skeletal system of the operator are derived and recorded from a force-sensing device. Further, an angle or position sensor is situated in contact with the standing wheelchair or standing exercise system in such a manner that the standing angle of an individual or the angle of the standing wheelchair can be logged and stored for long periods of time. Muscle force, through electrical stimulation or voluntary exercise can also be logged and stored in both the standing wheelchair application and in the stationary standing frame application.

23 Claims, 7 Drawing Sheets

THERAPEUTIC EXERCISE SYSTEM AND METHOD FOR A PARALYZED AND NONPARALYZED NEUROMUSCULOSKELETAL TRAINING SYSTEM

BACKGROUND

The present invention relates to an exercise method for able-bodied individuals and for individuals who are suffering from muscular paralysis and who may or may not be confined to a wheelchair The use of electrical stimulation to activate paralyzed muscle groups as a mode of exercise is well known. Functional electrical stimulation (FES) has been found to increase the contraction speed of paralyzed skeletal muscles in addition to aiding in the prevention of the effects of atrophy and osteoporosis in the unused muscles and bones, respectively, of a paralyzed individual. Further, the use of exercise machines that provide an individual with the capabilities to perform isometric or isotonic exercises by the electrical stimulation of paralyzed muscles is also well known. However, the previous generations of exercise devices fail to provide an individual using the exercise machine the capability to actively stand on their own, and be supported within the device, while their muscle groups are being electrically stimulated for exercise under active or active resistive conditions.

Therefore, there is a need for an exercise device that can safely provide active and active resistive supported standing exercise options to persons who either have limited physical mobility or complete loss of mobility due to muscular paralysis.

There is also a need for a method to improve an individual's neuromuscular control following disuse, trauma, surgery, or from an unstable joint subsequent to ligament injury, disuse. The previous generations of exercise equipment do not apply a measurable resistance directly to the joint (ie back of the knee), which helps protect the joint by minimizing tangential forces (shear) and increasing compressive or axial loads.

SUMMARY

The present invention is a new and novel paradigm for the therapeutic exercise of the human neuro-musculoskeletal system for individuals that suffer from muscle paralysis or muscles that have been weakened or altered by diminished neuromuscular control or to re-train the muscles surrounding a joint or joints that have been debilitated by disuse from surgical repair, immobilization, trauma, fracture, or ligament laxity. For individuals who can activate their muscles voluntarily, the present invention allows for a method to exercise against programmable resistances to assist with relearning neuromuscular control at a given joint or joints or exercising without the fear of a fall because of balance problems (elderly). Rehabilitation after anterior cruciate ligament injury/reconstruction or for active exercise of the elderly with balance problems is an application of this invention. Alternatively, if the individual is completely paralyzed, then an external activation system (electrical stimulation) serves as the source of activating the muscles.

Moreover, this system provides the following two unique methods: 1) to quantify the synergistic strength of multiple muscles that cross the joint (such as the knee via the quadriceps and hamstring muscles) and 2) to adjust, under software control, the various resistances while flexing and extending the joint or joints under standing or other postural conditions.

An exemplary embodiment of the present invention relates to a therapeutic system that uses exercise to apply loads to the bone and muscle of individuals with paralysis. For this embodiment the system includes a rigid frame structure. Attached to the rigid frame structure of the exercise system is a stimulation device. The stimulation device is used to induce functional standing in a system operator by providing graded electrical stimulation to targeted paralyzed musclesof the system operator. The system also has the capability to accumulate operator position data, wherein the data is indicative of the physical standing position angle of the system operator's body within the exercise system or provides specific information about the angle that a standing wheelchair is placed. Also attached to the rigid frame structure is a passive restraint device. The passive restraint device is an important safety element that aids to position an operator within the rigid frame structure in addition to providing support to the operator if the electrically stimulated muscle groups of the operator fail and the operator is no longer able to maintain a functional electrically induced standing position. Resistive forces can be applied to the stimulated muscles of the standing system operator via a mechanical resistance device. A force sensor is used to measure the resistive force to the specific targeted paralyzed musculoskeletal complex group that the system operator wishes to load while in an active standing position.

Feedback data is collected from the stimulation device and the force application device and subsequently stored within a data storage system. The exercise system also includes a processor that is in communication with the stimulation device, the mechanical resistive device and the data storage and logging system. The processor can include one or more processing elements that are programmed or adapted to receive electrical activation power levels and operator position data from the stimulation device and force feedback data from the force sensing system in addition to transmitting commands to the stimulation device and the mechanical resistance device.

The accumulated data (e.g., the position or angle data, from which, velocity and acceleration can be derived, force, muscular electrical stimulation level etc.) that pertains to a system operator's exercise movements are transmitted to the processor. Intelligent motor control algorithms are implemented by the processor to process the data and to interactively determine and control both the stimulation parameters of the stimulation device and the resistance applied by the mechanical resistance device and measured by the force sensor in such a way that the targeted movement or type of muscle contraction may occur in a manner deemed most beneficial to the system operator.

A further exemplary embodiment of the present invention relates to a method for using an exercise system that targets the paralyzed musculoskeletal complex groups of an individual. The method includes the step of modulating the electrically stimulated activation of a paralyzed human muscle group in order to induce and facilitate functional standing and optimal lower extremity loading within an individual. As such, the axial (compressive) and tangential (shear) loads that are exerted on the skeletal system are derived from the force sensor measurements. Optimal lower extremity skeletal loads are defined as compressive loads and low shear or tangential loads at a threshold that has been shown to improve bone density during spaceflight and unloading. Optimal muscle forces are those forces that induce adaptations that enable the muscle to change in size and perform more work. Further, the method includes the step of providing passive standing support of an individual that is using the system in the event that the targeted electrically stimulated muscle group fails or the electrical stimulation system is not able to maintain the electrical stimulation activation of the system operator. The system determines the optimal muscle stimulation method of a targeted muscle group by utilizing force, position or angle (depending on the specific emobodiment), velocity and acceleration feedback data accumulated from the system, and storing the force, position or angle, velocity and acceleration feedback data accumulated from the system within a means of storage. Based on changes of these measures, various electrical stimulation protocols can be delivered and assessed as to the effectiveness in preventing muscle fatigue.

A yet further exemplary embodiment of the present invention relates to a therapeutic system for the exercise of targeted paralyzed musculoskeletal complex groups that includes a standing wheelchair device. The standing wheelchair is used to passively restrain, position and support a system operator. The axial (compressive) and tangential (shear) loads that are exerted upon the skeletal system of a system operator are computed from a horizontal force-sensing device. Further, a position or chair angle sensor is situated in contact with the standing wheelchair in such a manner that the sensor can determine the standing angle of an individual that is confined within the standing wheelchair. The position or angle sensor measures the plane of the angle that the standing wheelchair is positioned. The position or angle sensor data, muscle forces, and estimated loads are data logged and stored in the miniaturized portable microprocessor controlled system. Upon download to the host computer, the information stored during use of the chair can be retrieved and analyzed under software control.

The feedback data collected from the data logger is transmitted to a host computer and stored within a data storage system. The portable processor is in communication with the standing wheelchair and the data storage system, wherein the processor comprises one or more processing elements that are programmed or adapted to receive system operator position or angle data from the position or angle sensor, force feedback data from the force sensing device and/or transmit stimulation activation commands to the stimulation device. The standing wheelchair operator is additionally provided with a display device. The display device is in communication with the processor, and the standing wheelchair operator can view data that corresponds to the amount of load that is being placed on the wheelchair operator's extremities as well as the time, date, and number of bouts for standing. Thus, the total work performed is provided as feedback to the operator so that the dose of loading can be prescribed, measured, and a determination made if the operator is complying with the prescribed dose.

Another exemplary embodiment of the present invention is in the therapeutic use for the rehabilitation of individuals with anterior cruciate ligament injury/surgery. Because of the joint instability from orthopedic or neurological trauma, the goal of rehabilitation is to teach neuromuscular control so that both the quadriceps and hamstrings contract together across the knee (synergist). The present invention promotes the development of neuromuscular control by allowing programmable resistances to be applied throughout the range of joint motion to improve neuromuscular control of the joint. For this application, the system does not require the passive resistive elements to support the stance of the operator nor does it require an electrical stimulation system.

The operator will actively contract the leg muscles of one or both knees in order to move from a partial squat to an upright standing position. The mechanical resistance device, under programmable software control, introduces various resistances ranging from no resistance (less challenging) to highly random resistances (most challenging) during each movement. The operator attempts to move at a predetermined rate and distance provided by a visual display on a computer screen. The operator's ability to follow the prescribed position is determined by comparing the actual position sensor response to the predetermined position displacement displayed on the computer monitor. A score signifies how successful the operator could control the knee during the graded resistive tasks. This invention enables the operator to exercise multiple muscle groups during a functional single limb or double limb partial squat, but in addition enables the operator to measure their skill during these controlled movements under highly unpredictable resistances under software control.

A final exemplary embodiment of the present invention is its therapeutic use for the elderly with balance problems. For this embodiment, the passive support system would be required but the muscle activation system would not be required. Elderly confined to a nursing home or living at home who would like to experience voluntary graded resistive exercise in an upright position but are hesitant due to balance problems are ideally suited for this invention. In this application, the appropriate resistance can be dialed in manually or be controlled by a computer system. The operator is able to exercise while receiving a visual display of the work performed which also is stored to quantify change. In the event the individual stops activating the muscles or loses their balance, the passive standing system maintains them in an upright posture. This would provide the operator a level of independence during exercise.

BRIEF DESCRIPTION OF DRAWINGS

The accompanying drawings, which are incorporated in and constitute a part of this specification, illustrate embodiments of the invention, and together with the description, serve to explain the principles of the invention.

DETAILED DESCRIPTION

Embodiments of the invention are described below in detail. The disclosed embodiments are intended to be illustrative only since numerous modifications and variations therein will be apparent to those of ordinary skill in the art. In reference to the drawings, like numbers will indicate like parts continuously throughout the views. As used in the description herein and throughout the claims that follow, the meaning of "a," "an," and "the" include plural references also, unless the context of use clearly dictates otherwise. Additionally, the meaning of "in" includes "in" and "on" unless the context clearly dictates otherwise as the term is used in the description herein and throughout the claims that follow.

The presently described invention integrates the passive support of an exercise system operator with the electrically induced active standing of a system operator and optionally allows for the application of a resistive force to the electrically stimulated muscles of the system operator to facilitate the exercising of the system operator's paralyzed leg muscles. Therefore, individuals with paralysis can be provided with the ability to stand under the active control of their own musculature and complete a repetitive exercise regimen against a fixed or variable resistive force. There is a corollary effect between the muscle forces generated by a standing system operator and the load applied to the operator's skeletal system; the greater the generated muscle forces the greater the load applied to the skeletal system. Further, by increasing the cumulative sum of the force load to the bones, then the longer the muscles can generate a responsive force. The low force strains exerted to the limbs of a paralyzed individual are insufficient to prevent osteoporosis in the unused bones of the individual afflicted with paralysis.

The present invention provides fixed or variable resistance adjustments that assure higher loads are placed on the skeletal system of a paralyzed individual. Loads through the extremities are optimized to enhance the maintenance of musculoskeletal integrity following the paralysis of the musculature of an individual.

Figure 1:
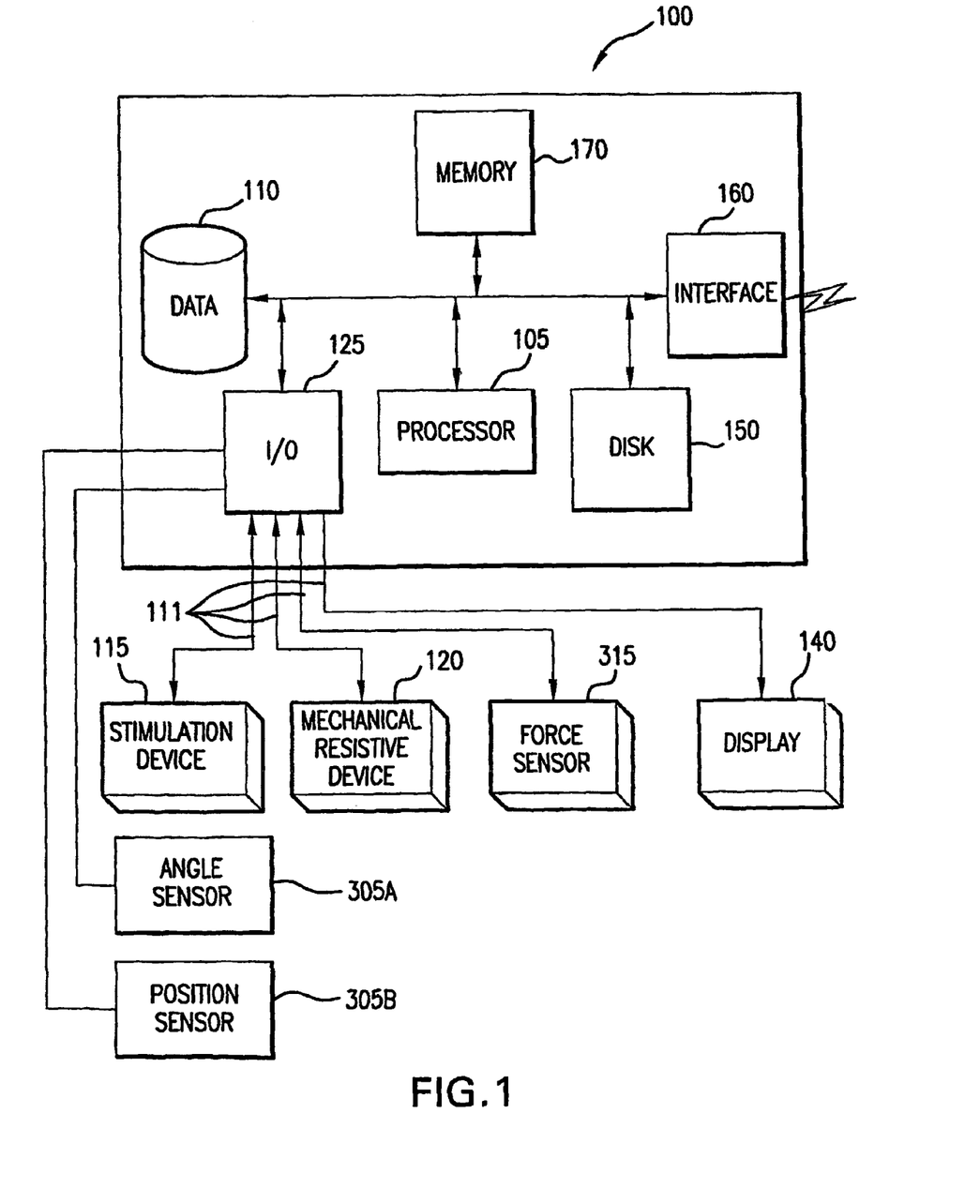
FIG. 1 illustrates computer system that can be used in the present invention.
Figure 2:
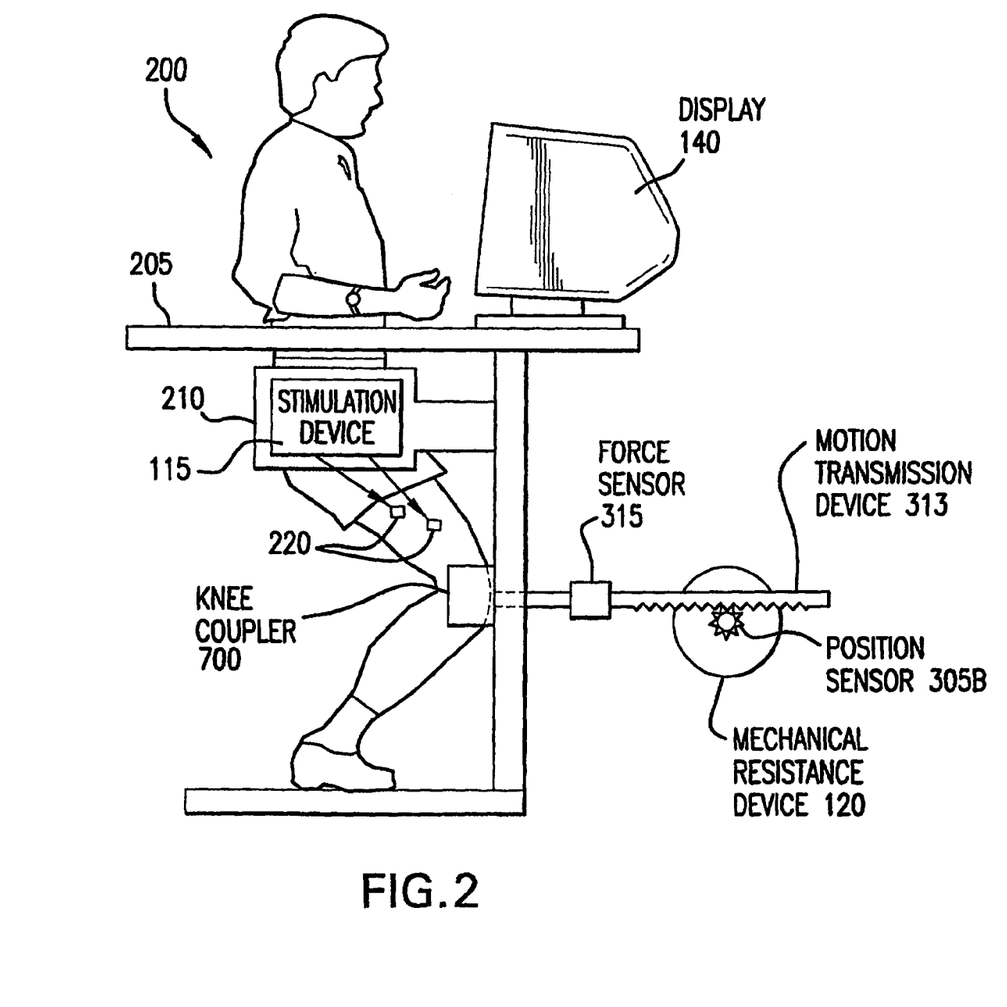
FIG. 2 illustrates an block diagram of the present invention.

The present invention is initially described in reference to FIGS. 1 and 2. FIG. 1 is a diagram that illustrates a computer system 100 that may be used in conjunction with the present invention. The computer or computer system 100 can be a conventional personal computer. Accordingly, to interface with the system operator, the computer system 100 includes a display device 140, which displays a user interface (not shown) that operates in accordance with conventional windowing graphical user interface (GUI) paradigms. The computer system 100 also includes hardware and software elements of the types generally used in conventional personal computers, such as a processor 105, a disk storage device 110 (e.g., a hard disk drive), an input/output interface 125, a network interface 160, and a removable read/write storage device 150 (e.g., a CD-ROM or a floppy disk drive). The computer system 100 further includes other hardware and software elements of the types conventionally included in personal computers, such as an operating system, but these elements are specifically not shown for purposes of clarity. Similarly, the software elements of the computer system 100 can be transferred from the computer system 100 to another destination via data transferred to a recordable media via the read/write storage device 150 or the network interface 160. Input data can be transmitted to the computer system 100 via communication channels 111.

As shown in FIG. 2, the stimulation device 115, the mechanical resistive device 120, motion transmission device 313, position sensor 305B, and force sensor 315 are integral components of the exemplary illustrated therapeutic exercise system (FIG. 2) 200. The exercise system 200 additionally includes a rigid frame structure 205, a passive restraint device 210 and electrode pads 220, which are physically associated with the stimulation device 115.

A system operator is positioned and secured within the passive restraint device 210 that is attached to the rigid frame structure 205. The passive restraint device 210 provides support to the system operator during an exercise period by allowing the system operator to passively stand within the rigid frame structure 205. Additionally, the passive restraint device 210 serves as a fail-safe support system in the event the electrical muscle stimulation provided by the stimulation device 115 to the system operator's muscles fails or, in the case of an elderly person, if they were to lose their balance. For example, if the desired exercise to be accomplished is the extending and flexing of the operator's knee while they are positioned in a stance, the operator is supported in such a manner that a passive upright standing condition can be achieved while the stimulation device 115 is used to produce the greatest therapeutic benefit. In the event that the stimulation device 115 fails, the system operator will be safely returned to a passively supported standing position.

As illustrated in FIG. 2, the electrode pads 220 are applied to the target musculoskeletal group of a system operator and an appropriate electrical stimulation is applied to the muscle group via the stimulation device 115 in order to induce functional active standing in the system operator. The stimulation device 115 has the capability to activate the muscles after which a separate interface has the capability to monitor and accumulate position data 305B or force data 315 that is indicative of the standing angle position of the system operator, and subsequently transmit this position data to the computer system 100. The exercise system 100 can use either open loop or closed loop control to modulate the electrical activation of the paralyzed muscle group and induce functional active standing within the system operator As mentioned above, the computer system 100 is in communication with the mechanical resistive device 120 (FIGS. 1 and 2) and the stimulation device 115 (FIGS. 1 and 2). The mechanical resistive device 120 has the capability to apply varying resistive forces to a targeted paralyzed musculoskeletal complex group of the system operator while the operator is actively or passively standing within the system. The processor 105 is programmed or adapted to receive operator position data from the angle or position sensor 305A, 305B and mechanical resistive information 120 and operator force feedback data from the force sensor device 315 in addition to transmitting stimulation activation commands to the stimulation device 115. Data that is received at the processor 105 is subsequently stored within the data storage system 110. The optimal method of activating a paralyzed muscle group can be determined via system feedback information data. For example force, as measured by the force sensing device 315 and velocity and acceleration, as derived from the position 305B or angle 305A sensor and other data pertaining to a system operator's exercise movements can be measured and transmitted to the processor 105. Intelligent motor control algorithms are implemented by the processor 105 to process data and to interactively determine and control both the stimulation parameters of the stimulation device 115 and the resistance applied by the mechanical resistance device 120 in such a way that the targeted movement or type of muscle contraction may occur in a manner deemed most beneficial to the system operator. Further exemplary aspects of the above-described invention enable the mechanical resistance device 130 to apply a fixed or variable resistive force to the targeted paralyzed musculoskeletal complex group of the system operator.

Figure 6:
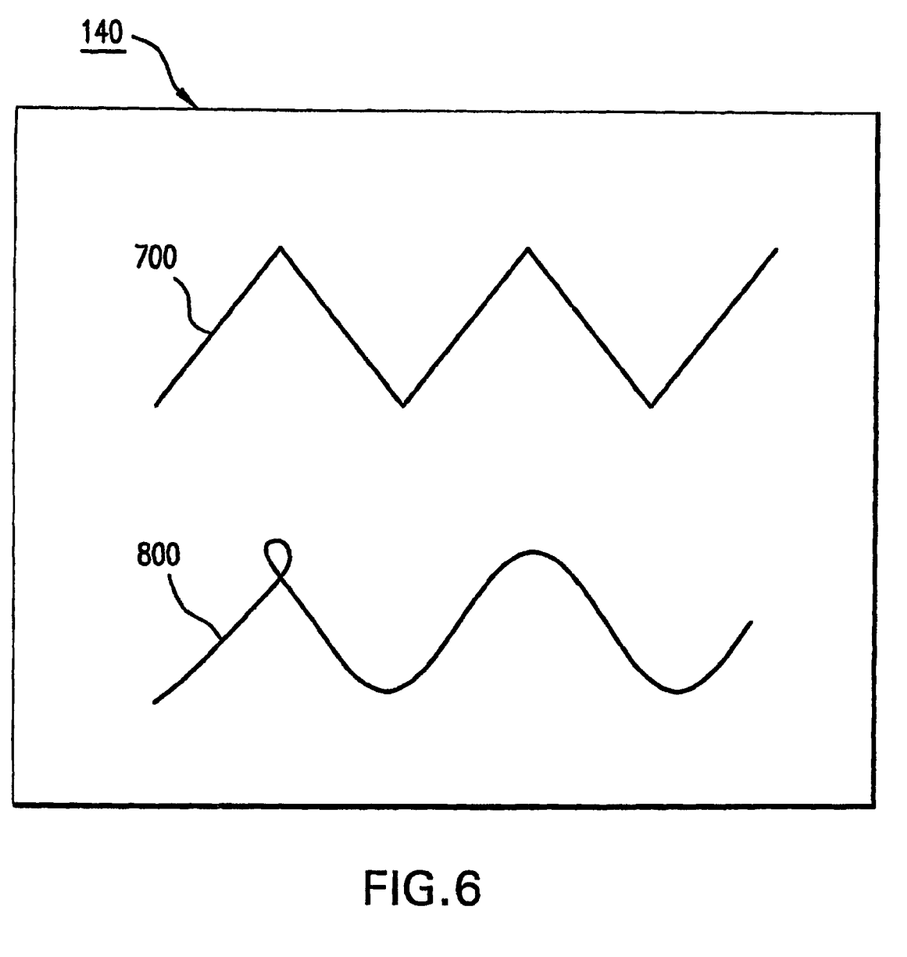
FIG. 6 illustrates one task via a display used to train the neuromuscular control system.

The same system, without the stimulation device 115, and with or without the rigid frame structure 205, can be used under volitional control. To teach a fixed movement to an operator the desired rate and magnitude of movement is displayed 140 for the operator (as shown in FIG. 6). The operator must strive to match the actual position or angle data displayed on a visual screen 140. The recommended movement 700 versus the actual movements 800 are displayed 140 and scored according to the success in following the prescribed movement. As such, graded challenges via the mechanical resistive device 120 can be introduced to challenge the "relearning" of muscle control around a joint debilitated by ligament instability, disuse, or trauma (FIG. 2). The same method of exercise, with the rigid frame structure 205, can be prescribed for those with balance difficulties (elderly).

Figure 3:
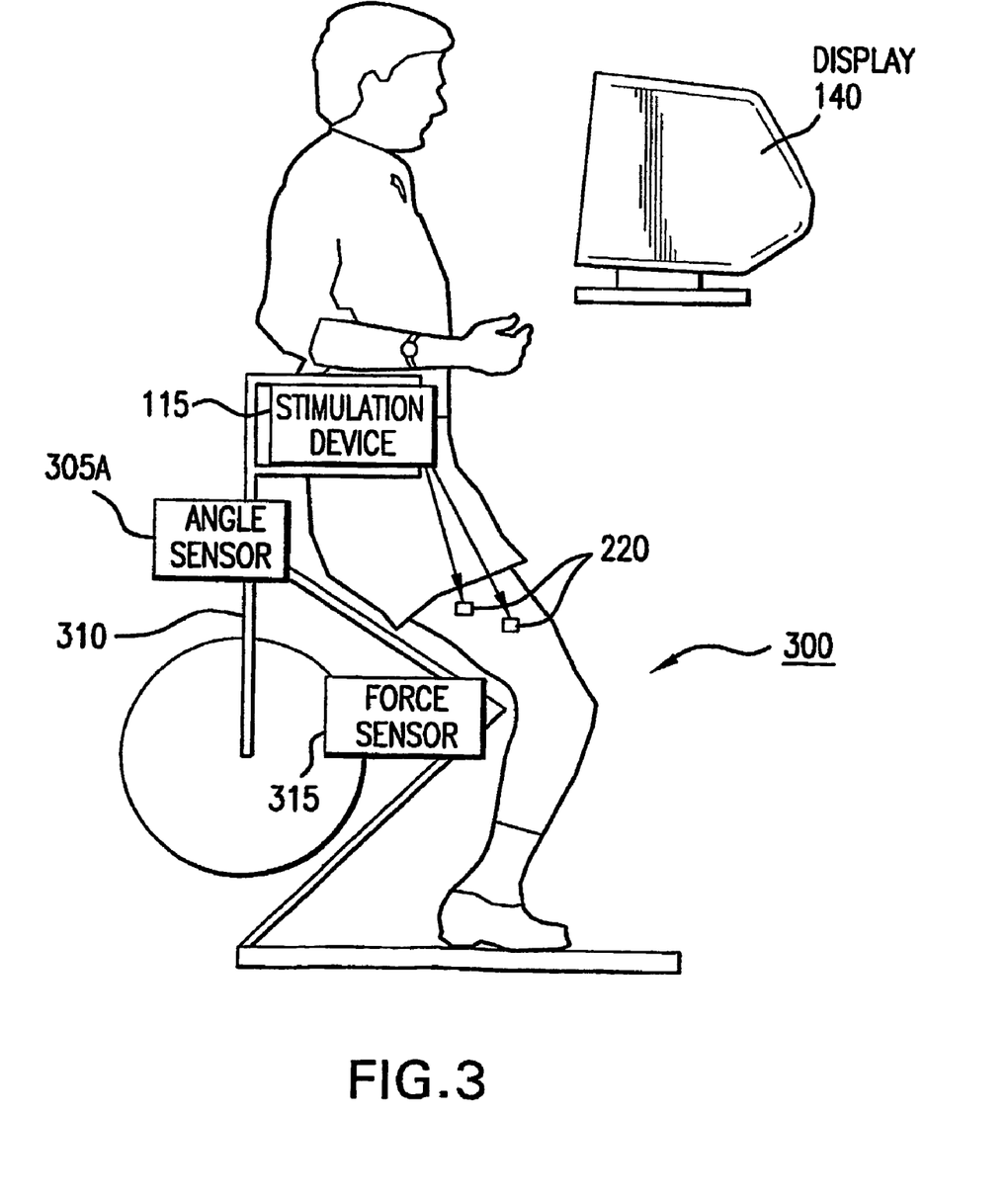
FIG. 3 illustrates an embodiment of the present invention that utilizes a standing wheelchair.

FIG. 3 illustrates a further exemplary embodiment of a therapeutic exercise system 300 that embodies a conventional standing wheelchair 310. The standing wheelchair 310 is used to passively restrain, position and support a standing wheelchair operator. The exercise system 300 further includes a stimulation device 115, an angle sensor 305A, a force-sensing device 315 and electrode pads 220 that are physically associated with the stimulation device 115. In alternative embodiments the angle sensor 305A and force sensing device 315 may be embodied in a single device.

The stimulation device 115 is used to induce active standing in a wheelchair operator, this is accomplished by placing the electrode pads 220 associated with the stimulation device 115 upon the target paralyzed muscle group (e.g., the quadriceps muscles of the system operator) and providing a graded electrical stimulation to the targeted paralyzed musculoskeletal complex group (FIG. 3). A battery-powered source (not shown) can be used to provide the power to the stimulation device 115 (FIG. 3).

The force-sensing device 315 is situated in contact with the standing wheelchair 310. The force sensing device 315 records the force and analyzes the axial and tangential loads that are exerted upon the skeletal system of a system operator while the operator is engaged in the exercise of induced active standing. The component axial and tangential forces placed on the bone can be estimated from the measured force via microporcessor 405 based firmware control FIG. 4).

Figure 4:
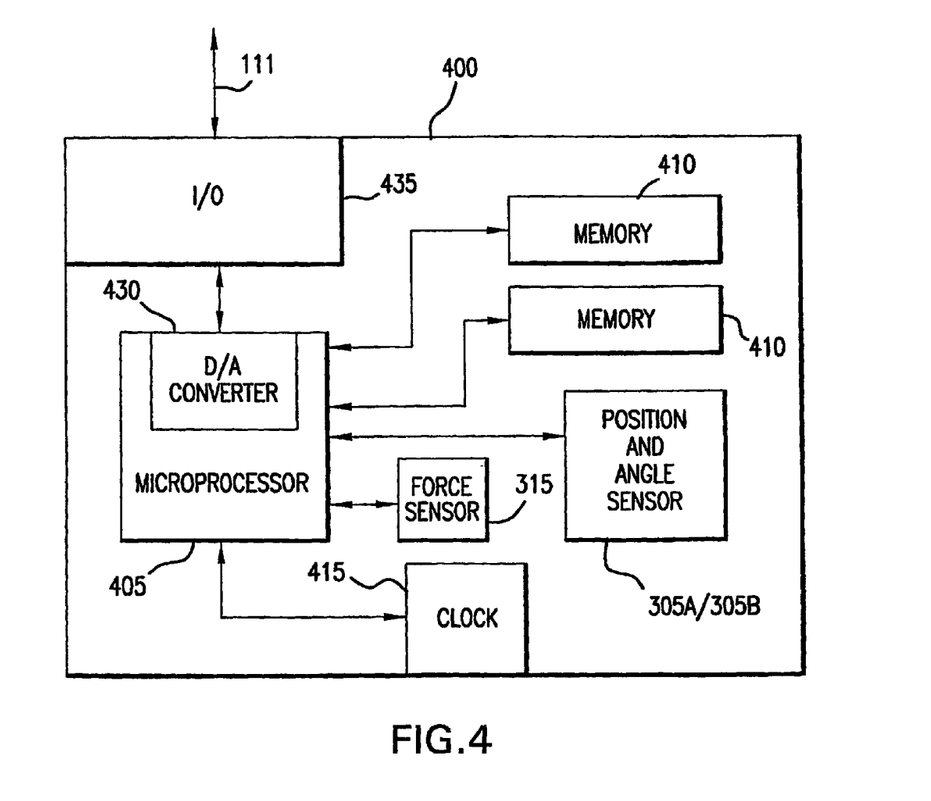
FIG. 4 illustrates an embodiment of a position and angle sensor used in the present invention.

The angle sensor 305A is also situated in contact with the standing wheelchair device in such a manner that the standing angle of the system operator can be determined and measured (FIG. 3). As shown in FIGS. 3 and 4, the position or angle sensor 305A 305B can embody any number of sensors. The angle sensor 305A provides an analog voltage that is proportional to the plane of the wheelchair seat The circuitry 310 of the position and angle sensors 305A 305B can embody a microcontroller IC 405, non-volatile EEPROM memory IC's 410, a real-time clock IC 415, a parallel port interface 435 and amplifiers (not shown) to acquire and processangle/position information and force information 315. Further, the microcontroller 405 embodies internal A/D converters 430 for the digitization of the angle and force data in addition to internal ROM code that can be used to implement data logging programs.

The angle and force data are sampled and periodically recorded to memory and digitally marked with a time and date stamp according to programmed criteria. The parallel port interface 435 allows the recorded angle and force data to be accessed and read by a host computer in addition to allowing the logging program to be controlled or programmed.

The data detected by the force-sensing device 315 and the position or angle sensor 305A and 305B is accumulated and transmitted to the computer system 100. The processor 105 uses the position or angle and force data to determine the shear and compressive loads that are being exerted on the bones of the system operator. The accumulated angle and force feedback data can also be displayed to the system operator on the display device 140. Further, the integral of the muscle force-time curve can be calculated and displayed to the system operator in order to provide the operator with information in regard to the amount of work that the operator has completed with each period of exercise.

Further aspects of the above mentioned invention allow for the optimal stimulation of the paralyzed musculoskeletal complex group by varying of the frequency, intensity and duty cycle of the applied electrical stimulation from the stimulation device 115. Further, the data transmitted from the force sensor 315 to the processor 105 can used to determine the percentage of a system operator's body weight that is being exerted through the system operator's extremities. The determined percentage of an operator's body weight that is being exerted through a system operator's extremities then can be used to determine the appropriate dosage of resistive load that should be exerted against the system operator's extremities in order to prevent bone loss.

Figure 5:
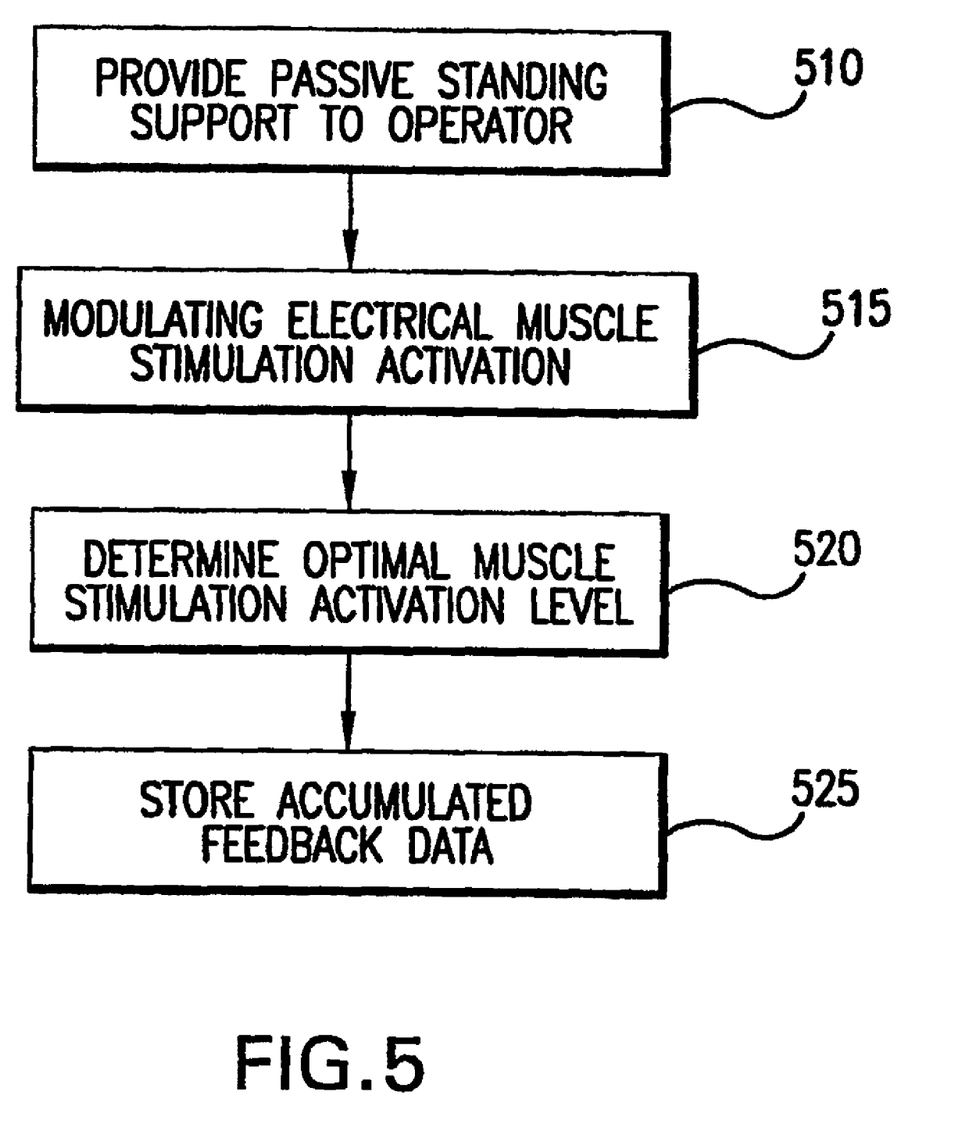
FIG. 5 depicts a method of using an exercise system relating to the present invention.

FIG. 5 illustrates an exemplary method for using an exercise system that targets paralyzed musculoskeletal complex groups. At step 510 the method dictates the providing of passive standing support of a system operator. The passive support is provided as a fail-safe in the event that an electrically activated muscle group fails or the electrical stimulation system is not able to maintain the electrically stimulated muscle group force of the system operator. If the operator is volitionally activating their musculature then the passive support would be of use for those with balance control problems (elderly). The paralyzed muscle group of the system operator is electrically stimulated at step 515 in order to induce functional standing and optimal lower extremity loading within the system operator. Further, at step 520, an optimal muscle stimulation electrical activation method is determined by utilizing force, position or angle information (from which velocity and acceleration can be derived) to feedback data accumulated from the system, and at step 525, the force, velocity and acceleration, and position/angle feedback data accumulated from the system is stored within a storage device.

Figure 7:
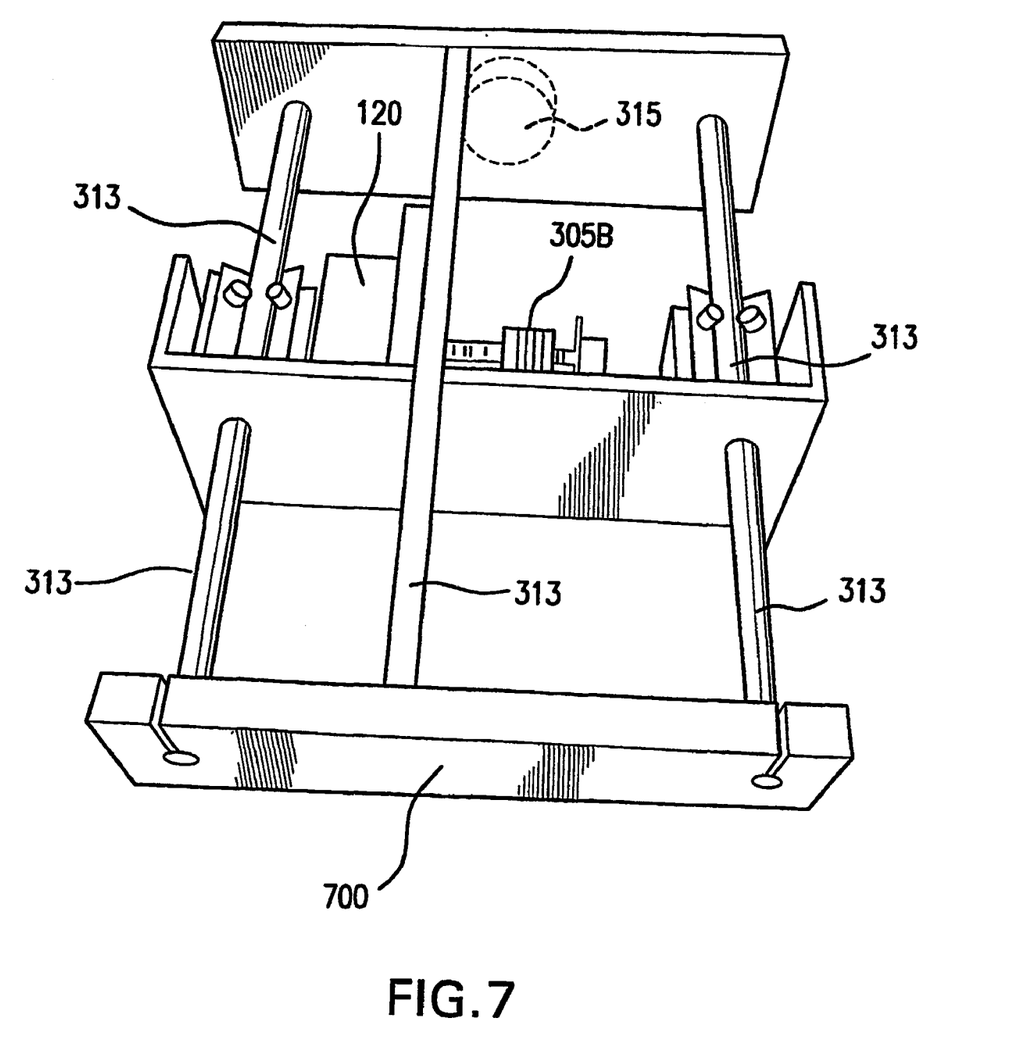
FIG. 7 is an illustration of sensors and mechanical resistive system integrated in one design.

A final example of the specific components of the neuromusculoskeletal exercise system is illustrated in FIG. 7. The motion transmission device 313, knee coupler 700, position sensor 305B, force sensor 315, and the mechanical resistive device 120 are integrated in this embodiment.

Other aspects of the invention may be found from the attached drawings and other related materials such as a detailed review of the various functions offered by the present invention, which are integral parts of this disclosure. Moreover, other embodiments of the invention will be apparent to those skilled in the art from consideration of the specification and practice of the invention disclosed herein. It is intended that the specification and examples be considered as exemplary only.

What is claimed:

1. A therapeutic system for the exercise of target paralyzed musculoskeletal complex groups comprising:
  a rigid frame structure;
  a stimulation device that is situated upon the rigid frame structure, wherein the stimulation device provides graded electrical stimulation to a target paralyzed musculoskeletal complex group in order to induce functional standing in a system operator, and further, has the capability to accumulate data that corresponds to the standing angle of the system operator within the system;

a passive restraint device that is attached to the rigid frame structure, wherein the passive restraint device is utilized to restrain an operator within the rigid frame structure and provide support to an operator in the event that functional electrically induced standing fails;

a force application device in communication with the stimulation device, wherein the force application device applies resistive force to the targeted paralyzed musculoskeletal complex group of the system operator;

a data storage system capable of storing various feedback data collected from the stimulation device and force application device;

a processor in communication with the stimulation device, the force application device and the data storage system via at least one communication channel, wherein the processor comprises one or more processing elements that are programmed or adapted to:
  a) receive operator position/angle data from a sensor
  b) receive resistive force feedback data from the force sensor device; and
  c) transmit activation commands to the stimulation device.

2. The system of claim 1, wherein the processor performs the additional steps of:
  d) controlling resistive exercise through a mechanical resistive device under computer control;
  e) interfacing the motion transmission device through a knee coupler; and
  f) Portably logging of position/angle, force, velocity, acceleration, muscle work completed, bone loads, time, date, and duration of standing.

3. The system of claim 1, wherein the optimal stimulation of the paralyzed musculoskeletal complex group is accomplished by the system varying the frequency, intensity and duty cycle of the applied electrical stimulation.

4. The system of claim 1, wherein the feedback data comprises data representing the force, velocity and acceleration of the mechanical resistive device.

5. The system of claim 1, wherein the force application device applies a fixed resistive force to the targeted paralyzed musculoskeletal complex group of the system operator.

6. The system of claim 1, wherein the mechanical resistive systemapplies a variable resistive force to the targeted paralyzed musculoskeletal complex group of the system operator.

7. The system of claim 1, wherein the system allows for an operator to actively stand while being supported against a variable resistance provided by the mechanical resistive device and sensed by a force sensor.

8. The system of claim 1, wherein the rigid frame structure and passive restraint device comprise a standing wheelchair device.

9. The system of claim 8, wherein the standing wheelchair device has the capability to monitor force, chair angle, muscle work, and the duration of time that a system operator has been standing.

10. The system of claim 8, wherein the standing wheelchair device transmits the monitored data to the processor and the data is used to determine the percentage of a system operator's body weight that is being exerted through the system operator's extremities.

11. The system of claim 8, wherein the determined percentage of a operator's body weight that is being exerted through a system operator's extremities is used to determine the appropriate dosage of resistive load that should be exerted against the system operator's extremities in order to prevent bone loss.

12. A method for the utilizing a system for the exercise of target paralyzed musculoskeletal complex groups comprising the steps of:
  providing passive standing support of a system operator in the event that an electrically activated muscle group fails or the electrical stimulation system is not able to maintain the electrical stimulation of an electrically stimulated muscle group;
  modulating the electrical stimulation activation of a paralyzed human muscle group in order to induce functional standing and optimal lower extremity loading;
  determining an optimal muscle stimulation electrical activation method by utilizing force, velocity and acceleration feedback data accumulated from the system;
  storing the position/angle, force, velocity and acceleration feedback data accumulated from the system.

13. A computer readable storage environment comprising one or more storage devices or media storing instructions that upon execution by a system processor cause the system process to manage and execute interactive profiles within a system in accordance with the method of claim 11.

14. A system for the exercise of paralyzed musculoskeletal groups comprising:
  a means of supporting, positioning, and protecting the exercising subject as necessary or desirable such as to allow the target musculoskeletal complex to be targeted;
  a means for producing and applying electrical muscle stimulation to the target musculature to produce graded muscle contraction as appropriate for a predetermined exercise mode and therapeutic goal;
  a means of applying controlled mechanical resistance to resist the action of a muscle, thereby controlling the motion of the target musculoskeletal complex;
  a means of producing integrated control of both a stimulating and resistance device to control the movement of the target musculoskeletal complex in the manner desired to produce a therapeutic exercise goal;
  a means of monitoring and storing system feedback data and subsequently transmitting the data back to a client so that optimal stimulation may occur;
  a means of monitoring and storing system feedback data and subsequently transmitting the data back to a client so that optimal daily skeletal bone loading may occur.

15. A therapeutic system for the exercise of target paralyzed musculoskeletal complex groups comprising:
  a standing wheelchair device, wherein the standing wheelchair device is utilized to passively restrain, position and support a standing wheelchair operator;
  a stimulation device, wherein the stimulation device provides graded electrical stimulation to a target paralyzed musculoskeletal complex group in order to induce active standing in a wheelchair operator;
  a force sensing device that records and analyzes the axial and tangential loads that are exerted upon the skeletal system;
  an angle or position sensor situated in contact with the standing wheelchair device in a manner such that the tilt sensor determines the standing angle of a system operator within the standing wheelchair device;
  a data storage system capable of storing various feedback data collected from the standing wheelchair device;

a processor in communication with the standing wheelchair and the data storage system, wherein the processor comprises one or more processing elements that are programmed or adapted to:
  a) receive operator position data from the tilt sensor;
  b) receive force feedback data from the force sensing device;
  c) transmit activation commands to the stimulation device;
a display device in communication with the processor, wherein data in regard to the amount of load placed on a standing wheelchair operator's extremities are displayed to the standing wheelchair operator.

16. The system of claim 15, wherein the optimal stimulation of the paralyzed musculoskeletal complex group is accomplished by the system varying the frequency, intensity and duty cycle of the applied electrical stimulation.

17. The system of claim 15, wherein the angle or position t sensor comprises an IC accelerometer, potentiometer, or other angle sensing device.

18. The system of claim 15, wherein angle or position and force data are periodically sampled and stored in a data storage system.

19. The system of claim 15, wherein the processor uses the position or angle and force data to determine the shear and comprehensive loads on a system operator's leg bones and transmits and displays this data to the operator at the operator console.

20. The system of claim 15, wherein the determined percentage of a operator's body weight that is being exerted through a system operator's extremities is used to determine the appropriate dosage of resistive load that should be exerted against the system operator's extremities in order to prevent bone loss.

21. The system of claim 15, wherein the integral of the muscle force-time curve is used to provide muscle work completion information to the system operator after an exercise session.

22. The system of claim 15, wherein the stimulation device is powered by a battery power source.

23. A system for the exercise of non-paralyzed musculoskeletal groups comprising:
  a means of supporting, positioning, and protecting the exercising subject as necessary or desirable such as to allow the target musculoskeletal complex to be targeted;
  a means of applying controlled mechanical resistance to resist the action of a muscle or muscles, thereby controlling the motion of the target musculoskeletal complex;
  a means of teaching integrated control of both a volitional activation of muscles to control a joint or joints against a mechanical resistance device of the target musculoskeletal complex in the manner desired to produce a therapeutic exercise goal;
  a means of monitoring, displaying, and storing system feedback data and subsequently transmitting the data back to a client so that performance of graded exercise tasks can be compared with a given prescribed exercise task;
  a processor in communication with the data storage system, wherein the processor comprises one or more processing elements that are programmed or adapted to:
    a) receive operator position/angle data from the position sensor;
    b) receive force feedback data from the force sensing device;
    c) transmit prescribed movement patterns and adjust commands to the mechanical resistive device so that the operator must learn to control the joint against unpredictable perturbations.

* * * * *